(12) United States Patent
Vogeli

(10) Patent No.: US 7,769,280 B2
(45) Date of Patent: Aug. 3, 2010

(54) CAMERA HANDPIECE

(75) Inventor: Peter Vogeli, Zurich (CH)

(73) Assignee: Volpi AG, Schlieren (CH)

( * ) Notice: Subject to any disclaimer, the term of this patent is extended or adjusted under 35 U.S.C. 154(b) by 245 days.

(21) Appl. No.: 11/720,080

(22) PCT Filed: Nov. 24, 2005

(86) PCT No.: PCT/CH2005/000697
§ 371 (c)(1),
(2), (4) Date: Oct. 8, 2007

(87) PCT Pub. No.: WO2006/056094
PCT Pub. Date: Jun. 1, 2006

(65) Prior Publication Data
US 2008/0204863 A1 Aug. 28, 2008

(30) Foreign Application Priority Data
Nov. 24, 2004 (CH) .................................. 1933/04

(51) Int. Cl.
*A61B 1/04* (2006.01)
*A62B 1/04* (2006.01)
(52) U.S. Cl. ......................................... 396/17; 348/65
(58) Field of Classification Search .................. 396/17, 396/73, 75, 79; 348/65, 345
See application file for complete search history.

(56) References Cited

U.S. PATENT DOCUMENTS

| 4,233,503 | A | * | 11/1980 | Saito | 250/204 |
|---|---|---|---|---|---|
| 5,113,261 | A | * | 5/1992 | Morisawa | 348/357 |
| 5,745,165 | A | * | 4/1998 | Atsuta et al. | 348/65 |
| 5,817,014 | A | | 10/1998 | Hori | |
| 6,370,334 | B1 | * | 4/2002 | Ishikawa | 396/132 |
| 6,478,730 | B1 | * | 11/2002 | Bala et al. | 600/121 |
| 6,638,216 | B1 | | 10/2003 | Durell | |
| 2002/0032367 | A1 | * | 3/2002 | Akiba | 600/127 |
| 2002/0151784 | A1 | * | 10/2002 | Mizoguchi et al. | 600/407 |
| 2002/0161279 | A1 | * | 10/2002 | Luloh et al. | 600/112 |
| 2002/0191098 | A1 | * | 12/2002 | Oshima | 348/345 |
| 2005/0264678 | A1 | * | 12/2005 | Butterworth | 348/345 |
| 2006/0206007 | A1 | * | 9/2006 | Bala | 600/182 |
| 2007/0223898 | A1 | * | 9/2007 | Purwanto | 396/17 |

FOREIGN PATENT DOCUMENTS

| DE | 19718189 | 2/1999 |
|---|---|---|
| DE | 19837404 | 2/1999 |
| DE | 19923122 | 11/2000 |
| DE | 19834207 | 4/2006 |
| WO | WO 02/062262 | 8/2002 |

* cited by examiner

Primary Examiner—Rodney E Fuller
(74) Attorney, Agent, or Firm—Sturm & Fix LLP

(57) ABSTRACT

A camera hand piece (1) with camera housing (12) has a microscopic probe (2) at the front end. On the rear side is a transmission cable (13) which is attached to the camera hand piece (1) with the aid of a coupling nut (14). The camera housing (12) accommodates a microscope housing (11) and includes a motorized drive (4), which drives an eccentric (7) via a gear (6) mounted in a gear housing (9). The eccentric (7) actuates a pusher (5), which moves a connecting rod (8) and thereby displaces a focusing lens system (3) attached to it in the axial direction. This axially displaceable focusing lens system (3) together with a condenser lens system (10), forms a microscopic lens system arranged in a microscope housing (11).

5 Claims, 1 Drawing Sheet

CAMERA HANDPIECE

BACKGROUND OF THE INVENTION

1. Field of the Invention

The present invention relates to a camera hand piece for a microoptical probe.

2. Description of the Related Art

Hand pieces of this kind are used for the electronic representation of microoptically generated images and their use in the medical sector is increasing, although they are also used in industrial technology.

For example, DE-199'23'122 describes a hand microscope for endoscopy, which uses the principle of the reflection of light to feed light through the microscope lens system into the area of the object. The image generated by the lens is digitized by an electronic image sensor, for example a CCD chip, and fed via appropriate connections to an evaluation unit for further processing and display. This hand microscope does not allow focusing and/or any possibility of altering the focal distance.

An endoscope with a manually operated control unit for the focusing and/or altering of the focal distance is known from DE-198'37'404 and/or DE-198'34'207. This can be operated with the thumb without having to remove the hand from the instrument. Unfortunately, this type of endoscopic instrument involves a complex mechanism that is difficult to maintain. In addition, these instruments have also proved to be extremely sensitive to temperature and cannot be easily sterilized in an autoclave.

In DE-197'18'189, it is suggested that the adjustable optical display system should be placed in its own housing section, whereby for focusing, the movable parts of the optical system mounted inside it can be moved in a rotary and/or translational manner by means of magnetic force transmission from outside with no contact involved.

Manual focusing and enlargement in all known systems leads to the displacement of images and requires further attention from the user, which is undesirable, in particular when observing medical operations.

It is therefore an object of the present invention to create a focusing camera hand piece for a microoptical probe, which is easy to maintain, i.e. has a simple construction, which is simple to clean, i.e. sterilize, and which is user friendly, i.e. does not require any particular attention from the user.

BRIEF SUMMARY OF THE INVENTION

The present invention solves this problem by means of a camera hand piece having a motorized miniature drive, which drives a pusher provided for the axial displacement of the focusing lens system via a miniature drive with an eccentric. The focusing lens system and the pusher (linkage bar) are connected to one another via a connecting rod. The miniature drive, the eccentric and the pusher are mounted in a transmission housing and can be easily disassembled. The motor drive can be activated or deactivated using an on-off switch. Preferably, this on-off switch is configured as a foot switch.

The camera hand piece can be disassembled and has a camera housing in which a condenser lens system that works together with the focusing lens system and a miniature CCD semiconductor element for the generation of the image signals are accommodated. The focusing lens system, which is displaceably mounted, and the condenser lens system, which is arranged fixed in the camera housing, form a miniature microscope optical system. The miniature CCD semiconductor element is an essential component of a video sensor. In addition, the camera housing comprises fastening means for a microoptical probe which can be detachably fastened.

In a preferred embodiment, the fastening means comprises at least one pivotably mounted spring clip attached to a plug-in pin. This spring clip is equipped with a catch element, which engages in a groove provided in the base of the probe, when a microoptical probe is plugged in.

BRIEF DESCRIPTION OF THE SEVERAL VIEWS OF THE DRAWINGS

The invention will now be described in greater detail using an exemplary embodiment and with the help of the drawings, in which.

DETAILED DESCRIPTION OF THE INVENTION

Figure 1:
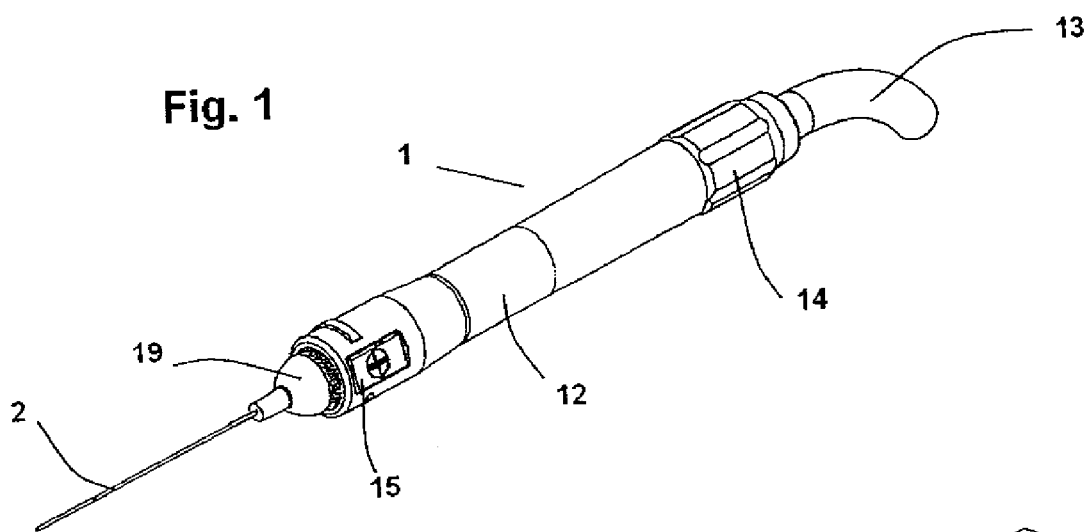
FIG. 1 shows a three-dimensional representation of the camera hand piece according to the invention.

The camera hand piece 1 shown in FIG. 1 essentially comprises a camera housing 12, to the front end of which a microoptical probe 2 is fastened. On the rear side, a transmission cable 13 is secured to the camera hand piece using a lock nut 14. The microoptical probe 2 can be plugged on in a simple manner with its base 19 and is secured using fastening means 15 in the form of a spring-loaded latch to the camera housing 12 such that it can be detached.

Figure 2:
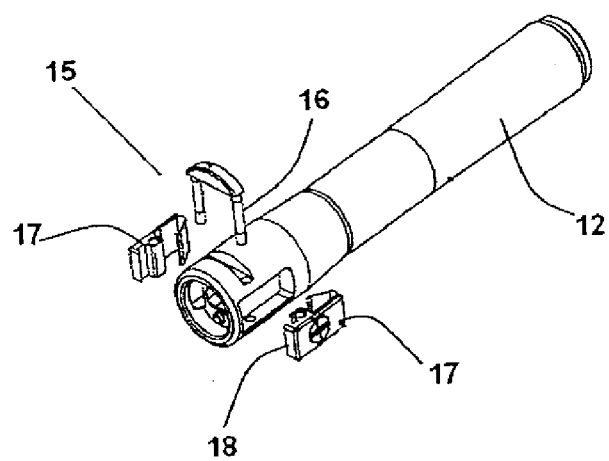
FIG. 2 shows a three-dimensional representation of a camera housing with fastening means according to the invention.

A particular embodiment of the fastening means used 15 can be seen in FIG. 2. These fastening means 15 have at least one plug-in pin 16, which reaches through the camera housing 12 into the pivot bearing of a spring clip 17. This spring clip 17 has a catch element 18 on the probe side, which engages with a nut provided in the base 19 of the microoptical probe 2 when the probe 2 is plugged in. This Figure shows clearly that the camera housing 12 and the fastening means 15 connected thereto are easy to disassemble and can be cleaned and reassembled without difficulty.

Figure 3:
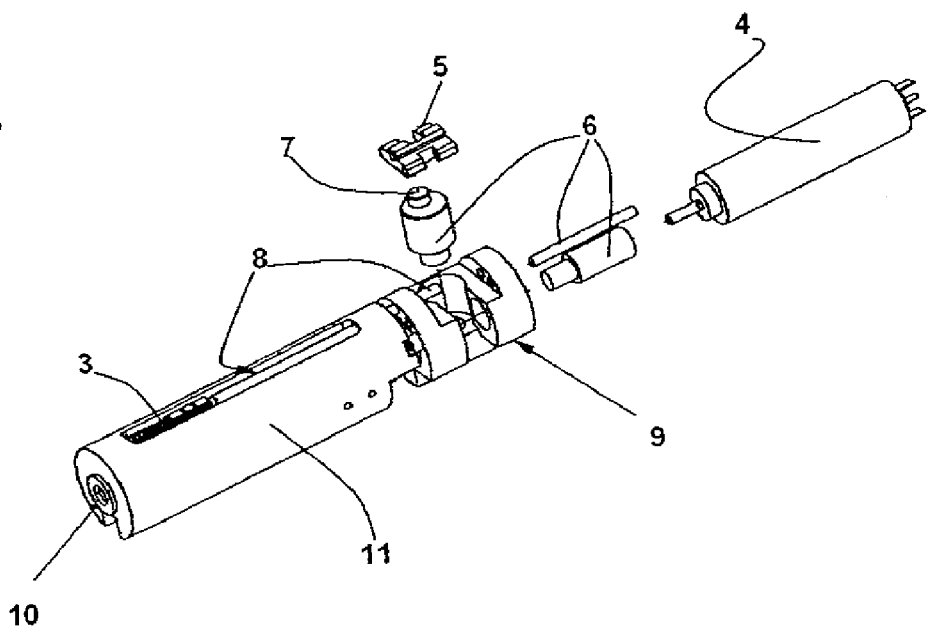
FIG. 3 shows a three-dimensional representation of the internal construction of a camera hand piece according to the invention.

FIG. 3 shows the internal construction of the camera hand piece according to the invention in a three-dimensional exploded view. This internal construction comprises a motorized drive 4, which actuates a pusher 5 by means of a gear 6 mounted in a gear housing 9 and an eccentric 7. This pusher 5 moves a connecting pin 8 and thereby a focusing lens system 3 secured to it on the probe side in the axial direction. A condenser lens system 10, together with the axially displaceable focusing lens system 3 (lens group), forms a microscope lens system, which is arranged in a microscope housing 11. It should be understood that the lens system of the microscopic probe 2 can be fastened with the aid of the fastening means 15 to the condenser lens system 10 such that it functions reliably. When activating the motorized drive 4, the gear member with the eccentric 7 is caused to rotate and thereby creates an axial back and forth movement of the pusher 5. This axial movement results in displacement of the focusing lens group 3 attached to the connecting pin 8. This enables the user easily to focus the object image without having to undertake laborious manual rotations of the hand piece.

This device is suitable for both the industrial and medical sectors. The advantages of this device will be immediately obvious to a person skilled in the art and in particular since the construction is simple to maintain, and since assembly and dismantling are easy, which allows the equipment to be sterilized in an autoclave, even by personnel not trained with the device.

It can be seen that the hand piece according to the invention is also suitable to use for medical laser treatment or in arthroscopy without any significant modifications. Further modifications can be made to the camera hand piece according to the invention by a person skilled in the art in order to adjust the hand piece for special usage purposes without thereby being inventive.

The invention claimed is:

1. Camera hand piece (1) for a microoptical probe (2) comprising, a focusing lens system (3) having a motorized miniature drive (4) which drives a pusher (5) provided for axial displacement of the focusing lens system (3) via a miniature gear (6) with an eccentric (7), wherein the focusing lens system (3) and the pusher (5) are connected to one another by means of a connecting pin (8), wherein the miniature gear (6), the eccentric (7) and the pusher (5) are mounted in a gear housing (9) such that they can be disassembled, wherein the focusing lens system (3) and a condenser lens system (10) cooperating with the focusing lens system (3) are stored in a microscope housing (11), wherein the microscope housing (11), the gear housing (9) and the motorized drive (4) are embedded in a camera housing (12), wherein the camera housing (12) has fastening means (15) for a microoptical probe (2) which can be detachable fastened, and wherein the fastening means (15) can be disassembled and has at least one spring clip (17) pivotably mounted on a plug-in pin (16).

2. Camera hand piece (1) according to claim 1, wherein the spring clip (17) has a catch element, which, when microoptical probe (2) is inserted, engages in a groove provided in the base (19) of said probe (2).

3. Camera hand piece (1) for a microoptical probe (2) comprising, a focusing lens system (3) having a motorized miniature drive (4) which drives a pusher (5) provided for axial displacement of the focusing lens system (3) via a miniature gear (6) with an eccentric (7), wherein the miniature gear (6), the eccentric (7) and the pusher (5) are mounted in a gear housing (9) such that they can be disassembled, wherein the focusing lens system (3) and a condenser lens system (10) cooperating with the focusing lens system (3), are stored in a microscope housing (11), wherein the microscope housing (11), the gear housing (9) and the motorized drive (4) are embedded in a camera housing (12), wherein the camera housing (12) has fastening means (15) for a microoptical probe (2) which can be detachable fastened, and wherein the fastening means (15) can be disassembled and has at least one spring clip (17) pivotably mounted on a plug-in pin (16).

4. Camera hand piece (1) according to claim 3, wherein the spring clip (17) has a catch element, which, when a microoptical probe (2) is inserted, engages in a groove provided in the base (19) of said probe (2).

5. Camera hand piece (1) for a microoptical probe (2) comprising, a focusing lens system (3) having a motorized miniature drive (4) which drives a pusher (5) provided for axial displacement of the focusing lens system (3) via a miniature gear (6) with a continuously driven eccentric (7), the focusing lens system (3) and a condenser lens system (10) cooperating with the focusing lens system (3), are stored in a microscope housing (11).

* * * * *